United States Patent [19]

Salamon et al.

[11] Patent Number: 4,659,834

[45] Date of Patent: Apr. 21, 1987

[54] PROCESS FOR THE PREPARATION OF FLUOROMETHYL-QUINOLINE DERIVATIVES

[75] Inventors: Zoltán Salamon; Ilona Imre née Virág, both of Tiszavasvári; Magdolna Sebestyén, Hajdunánás, all of Hungary

[73] Assignee: Alkaloida Vegyeszeti Gyar, Tiszvasvari, Hungary

[21] Appl. No.: 558,161

[22] Filed: Dec. 5, 1983

[30] Foreign Application Priority Data

Dec. 11, 1982 [HU] Hungary .............................. 4003/82

[51] Int. Cl.$^4$ .......................................... C07D 215/18
[52] U.S. Cl. .................................................... 546/180
[58] Field of Search ................................ 546/160, 167

[56] References Cited

U.S. PATENT DOCUMENTS

| 2,533,133 | 12/1950 | McBee | 546/180 |
| 3,412,095 | 11/1968 | Clark | 546/180 |
| 4,012,453 | 3/1977 | Hychka et al. | 546/180 |
| 4,277,607 | 7/1981 | Bulidon et al. | 546/180 |
| 4,429,130 | 1/1984 | Hickmann et al. | 546/167 |

FOREIGN PATENT DOCUMENTS 0049776  9/1981  European Pat. Off. .
909080  10/1962  United Kingdom .

OTHER PUBLICATIONS

Antimalarials II, Mar. 1968, Roger M. Pinder and Alfred Burger Dept. of Chemistry, Univ. of Virginia, Charlottesville, Va., pp. 267–269.
Derwent Abstract, BADI, Patent No. DE 2940-443, publ. Apr. 16, 1981.
J. Med. Chem. 14, 926 (1971).
Chem. Pharm. Bull 29(4) pp. 1069–1075, 1981.

Primary Examiner—Glennon H. Hollrah
Assistant Examiner—D. B. Springer
Attorney, Agent, or Firm—Karl F. Ross; Herbert Dubno

[57] ABSTRACT

A process is disclosed for preparing a compound of the Formula (I)

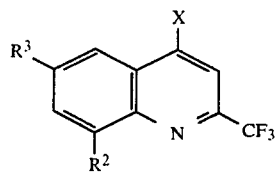

wherein
$R^2$ is trifluoromethyl or chloro;
$R^3$ is hydrogen or chloro; and
X is halogen; wherein a compound of the Formula (II)

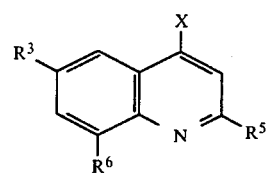

wherein
$R^5$ is —CFCl$_2$, —CF$_2$Cl, or —CCl$_3$; and
$R^6$ is chloro or trichloromethyl;

is fluoroinated either with a mixture of antimony (III) fluoride and antimony (V) chloride or bromide; or with antimony (V) fluoride; or with antimony (V) chloride and hydrogen fluoride.

4 Claims, No Drawings

PROCESS FOR THE PREPARATION OF FLUOROMETHYL-QUINOLINE DERIVATIVES

CROSS REFERENCE TO RELATED APPLICATIONS

This application is related to Applicants' copending application Ser. No. 557,106 filed Dec. 1, 1983 U.S. Pat. No. 4,599,349 issued 07/08/86.

In the past 15 years the importance of quinoline derivatives containing fluorine has increased rapidly. E.g. antimalarial (J. Med. Chem. 14 926, 1971) and analgesic derivatives (Chem. Ther. 1973, 2, 154–168) are known. The 4-halo-(tri)fluoromethyl-quinoline derivatives are important intermediates in the preparation of these compounds. The present invention provides a new, economical process readily usable on an industrial scale for the preparation of these compounds.

According to the literature these compounds were prepared by the following methods up to now:

When starting from compounds containing fluorine, such as trifluoromethyl-aniline, ethyl-trifluoroacetoacetate, generally the classical quinoline syntheses were applied (J. Het. Chem. 2 113, 1965; J. Med. Chem. 11 267, 1968; J. Het. Chem. 9, 1403–5, 1972).

These processes generally provided the desired compound with a low or medium yield; on the other hand the starting compounds containing trifluoromethyl substituent are rather expensive. Owing to the low or medium yields, a significant quantity of waste difficult to eliminate and containing organic fluorine is formed which gives rise to difficulties for the environment.

Other authors (Tetrahedron Lett. 1969 4095; Chem. Pharm. Bull. 18 2334–9, 1970) obtained trifluoromethyl-quinoline by reacting iodine and bromine quinolines under the conditions of an Ullman-reaction with trifluoro-iodine-methane in the presence of copper powder.

The yield is low or medium and the reaction has to be performed at a high temperature with trifluoromethyl-iodide gas which is not easy to prepare and difficult to treat. On the other hand only a moderate yield may be attained when using the expensive iodine-quinoline which is difficult to prepare.

Similarly, starting from the expensive, quinoline-carboxylic acids which are also difficult to prepare (e.g. homoaromatic carboxyl-substituted quinoline derivatives), a trifluoromethyl-quinoline derivative was obtained when the starting material was reacted with sulfur tetrafluoride in liquid hydrogen-fluoride. (Chem. Pharm. Bull. 17 2335–2339, 1969).

That process provides a rather low yield and the use of the sulfur tetrafluoride makes it difficult and complicated.

According to our best knowledge up to now a single quinoline derivative, the 2-trifluoromethyl-quinoline, has been prepared starting from trichloromethyl- and, resp., tribromo-methyl quinoline (U.S. Pat. No. 2,432,393) applying a known fluorination method (Bull. Acad. Roy. Belg. 35 375–420, 1898). However, the reaction conditions, the yield and the physical characteristics of the obtained product were not disclosed.

This invention relates to a process for the preparation of new quinoline dervatives of general formula (I),

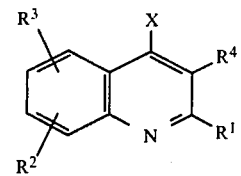

wherein
$R^1$ is a —$CF_3$, —$CF_2Cl$, —$CFCl_2$, —$CCl_3$, —$CF_2Br$, —$CFBr_2$, —$CBr_3$ group,
$R^2$ stands for hydrogen or halogen, a $C_{1-4}$ alkyl group or $R^1$ such that $R^1$ and $R^2$ cannot simultaneously stand for —$CCl_3$ or $CBr_3$,
$R^3$ is hydrogen or halogen or a $C_{1-4}$ alkyl group,
$R^4$ means hydrogen or halogen,
X represents halogen-by fluorinating the quinoline derivatives of formula (II),

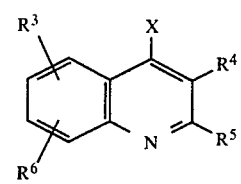

wherein
$R^3$, $R^4$ and X are as defined above,
$R^5$ is defined as $R^1$
$R^6$ is defined as $R^2$ but so that $R^5$ and $R^6$ do not simultaneously stand for —$CF_3$ and applying preferably antimony fluorides or hydrogen fluoride, the latter in the presence of a catalyst, as fluorinating agent.

$R^1$ to $R^6$ and X are always defined as above.

The compounds of the invention may be used as intermediates.

According to the invention, the inexpensive trichloromethyl- and, resp., tribromomethyl-quinolines are chosen as starting material (obtained by chlorination or bromination from methyl-quinolines which again are easily prepared from inexpensive basic material with good yields).

If hydrogen fluoride is used for the fluorination, as catalyst the halogenides of semi-metals or transition metals having a higher oxydation state are preferably used.

As fluorinating agent antimony fluorides, too, may be used. If antimony(V)-fluoride is used, a solvent is preferably applied and the process is carried out at a temperature of (−20) to (+30)°C. The fluoride is used in a quantity of 0.25 to 0.38 mole related to the chlorine or bromine atoms to be replaced in the halomethyl groups of the starting quinoline derivatives.

A good yield may be obtained if the reaction is performed in the presence of a halogenated hydrocarbon, e.g. dichloromethane, as solvent at a temperature of (−5) to 0° C.

The advantage of this process is that if the reaction mixture is treated with dry hydrogen-fluoride gas the antimony-fluoride may be regenerated. This fact improves the economy of the process.

According to the invention the fluorination may be carried out with mixed fluorides in the mixture of antimony(III) and antimony(V)-fluoride-chloride or -fluoride-bromide when the molar ratio of antimony(III) and antimony(V) is 1-5:1 and the ratio of fluorine-chlorine or bromine is 0.8-3.0 and the fluorine content of the reactant—related to the halogen atoms to be replaced—is 1.1 to 2.8 mole equivalents. The reaction is advantageously carried out at a temperature of 40 to 180, preferably at 100° to 160° C.

The fluorinating agent may be prepared e.g. by admixing e.g. antimony(III)-fluoride and antimony(V)-chloride or reacting a calculated quantity of chlorine or bromine with antimony(III)-fluoride and by the reaction of chlorine or bromine and hydrogen-fluoride as well as antimony(III)-chloride.

The transformation is influenced by the ratio of antimony(III):antimony(V) and that of fluorine:chlorine or fluorine:bromine.

Using the above ratios the halogenation in the nucleus and the tar formation may be reduced; the product may be easier isolated and the yield significantly improved.

From the aspect of the industrial application, the recognition that the desired transformation may be carried out with good yield by the aid of dry hydrogenfluoride in the presence of semi-metals of a higher oxidation state or transition metal-halogenides as catalysts is particularly significant.

For the fluorination as fluorine source hydrogenfluoride may be advantageously used in a quantity of 2-10, preferably 3-5 mole equivalents, in a solvent or without it, performing the reaction in the presence of 0.001-3.5, preferably 0.3-0.6 moles of semi-metal or transition metal-halogenide catalyst (related to the moles of the starting quinoline derivative) at a temperature of ($-10$) to ($+180$) °C., preferably at 60° to 120° C.

The process of invention is detailed by the following examples.

EXAMPLE 1

2-(Fluoro-dichloro-methyl)-8-methyl-4-chloro-quinoline 3.0 g of 2-trichloromethyl-8-methyl-4-chloro-quinoline are dissolved in 45 ml of dry dichloromethane and under intense stirring 1.5 ml of antimony-penta-chloride and 1.0 ml of antimony-penta-fluoride are added by dropping at a temperature of $-5°$ to $0°$ C. The mixture is stirred at this temperature for 4 hours and allowed to stand at room temperature for 48 hours. 6 ml of icy concentrated hydrochloric acid are added, the precipitate is filtered, washed with some dichloromethane, the filtrate is separated, dried, filtered and evaporated. 2.1 g solid product are obtained which is recrystallized from heptane: 1.9 g of a yellowish crystalline substance, 68.2%, m.p.: 90°-94° C.

The same way following compounds may be prepared: 2-(Fluoro-dichloromethyl)-4,6,8-trichloro-quinoline
M.p. 67°-72° C.

EXAMPLE 2

2-(Chloro-difluoromethyl)-8-methyl-4-chloro-quinoline

The mixture of 3.6 g of antimony-tri-fluoride and 0.5 ml of antimony-penta-chloride is heated under stirring to a temperature of 150° C. and stirred at this temperature for 5 minutes, then again cooled to 115° C., 2.95 g of 2-trichloromethyl-8-methyl-4-chloro-quinoline are added and stirred at a temperature of 110° to 120° C. for one hour. The reaction mixture is poured onto icy concentrated hydrochloric acid, extracted by chloroform, the organic phase is dried, evaporated, the residue is extracted by $4\times 50$ ml of heptane, the heptane phase is filtered and evaporated. 1.95 g oil are obtained by crystallizing while standing.
Yield: 74.4%
M.p.: 46°-48° C.

The same way following compounds may be prepared. 2-(Chloro-difluoromethyl)-4,6,8-trichloro-quinoline
M.p.: 32°-34° C.

EXAMPLE 3

2-Trifluoromethyl-8-methyl-4-chloro-quinoline

With a mixture of 3.6 g of antimony-trifluoride and 0.5 ml of antimony-penta-chloride obtained according to the previous example, 2.33 g of 2-trichloromethyl-4-chloro-8-methyl-quinoline are reacted. The reaction time is 30 minutes at a temperature of 150°-160° C. Isolation is carried out according to the previous example.

Yield: 1.52 g; 78.3% of a yellowish liquid which may be purified by vacuum distillation.
Boiling point$_{18-22\ torr}$: 155°-165° C.

Following compounds may be prepared as above:

|  | M.p.: |
| --- | --- |
| 2-Trifluoro-methyl-4,6,8-trichloro-quinoline | 71-73° C. |
| 2-Trifluoro-methyl-4-chloro-quinoline | 33-35° C. |
| 2-Trifluoro-methyl-6-methyl-4-chloro-quinoline | 66-68° C. |
| 2-Trifluoro-methyl-6,8-dimethyl-4-chloro-quinoline | 102-104° C. |
| 2-Trifluoro-methyl-4,8-dichloro-quinoline | 58-59° C. |
| 2-Trifluoro-methyl-6-bromo-4-chloro-quinoline | 93-95° C. |
| 2-Trifluoro-methyl-6-fluoro-4-bromo-quinoline | 96-98° C. |
| 2-Trifluoro-methyl-4,6-dichloroquinoline | 100.5-102.5° C. |

EXAMPLE 4

2-Trichloromethyl-8-difluorochloromethyl-4-chloro-quinoline

A mixture of 2 g of 2,8-bis(trichloromethyl)-4-chloro-quinoline, 4 ml of anhydrous hydrogenfluoride and 0.01 ml of antimony-pentachloride is kept in a closed teflon tube at a temperature of 100° C. for 48 hours. The mixture is poured onto the mixture of 100 g of ice and sodium hydrogen carbonate, extracted with $3\times 50$ ml of chloroform, dried over magnesium sulfate and evaporated. The residue is triturated with some petroleum ether and filtered off.
Yield: 1.65 g, m.p.: 71°-73° C.

EXAMPLE 5

A mixture of 1 g of 2,8-bis(trichloromethyl)-4-chloro-quinoline, 1.5 g of antimony-trifluoride and 5 ml of monochlorobenzene is heated under reflux for 18 hours. It is recooled, extracted by 10 ml of 10 percent hydrochloric acid and 10 ml of water, dried, filtered and evaporated. The residue is recrystallized from petroleum ether.
Yield: 0.62 g, m.p.: 69°-71° C.

EXAMPLE 6

2-Trichloromethyl-8-trifluoromethyl-4-chloro-quinoline 3.98 g of 2,8-bis-trichloromethyl-4-chloro-quinoline are dissolved in 10 ml of dichloromethane. A mixture of 1 ml of antimony-pentafluoride and 40 ml of dichloromethane are dropped at room temperature under stirring within 2.5 hours. The mixture is stirred at room temperature for 4 hours and 50 ml of 10 percent hydrochloric acid are added. The two phases are isolated, the organic phase is washed by 50 ml of water, dried over sodium sulfate and evaporated. The obtained substance (4.0 g) is extracted by 3×50 ml of hot hexane, filtered and evaporated. The residue is recrystallized from 80 percent methanol.

Yield 2.0 g, m.p.: 84°–86° C.

EXAMPLE 7

2-Difluoro-chloromethyl-4-chloro-8-trifluoromethyl-quinoline

A mixture of 2 g of 2,8-bis(trichloromethyl)-4-chloro-quinoline, 4 ml of anhydrous hydrogen-fluoride and 0.1 ml of antimony-pentachloride is kept at a temperature of 150° C. for 40 hours. It is poured onto the mixture of 100 g of ice and sodium hydrogen carbonate, extracted with 3×50 ml of chloroform, dried over magnesium sulfate and evaporated. The residue is triturated with some petroleum ether and filtered. The obtained 1.2 g of crystalline substance is purified by chromatography by the aid of a column filled with 40 g of Kieselgel-60 and eluated with cyclohexane. Evaporating the combined identical fractions 0.2 g of 2-mono-fluoro-dichloro-methyl-4-chloro-8-trifluoro-methyl-quinoline and 0.7 g of 2-difluoro-chloro-methyl-8-trifluoro-methyl-4-chloro-quinoline are obtained.

M.p.: 37°–39° C.

EXAMPLE 8

11.8 g of 2-trichloromethyl-8-trifluoro-methyl-4-chloro-quinoline are dissolved in 30 ml of dry dichloromethane and the mixture is cooled to −5° C. At a temperature of −4° to −6° C., 1.8 ml of antimony-pentafluoride are dropped within 40 minutes. The mixture is stirred for further 3.5 hours at this temperature, then 30 ml of icy concentrated hydrochloric acid are admixed. The organic phase is washed with 50 ml of water, then dried, filtered, evaporated, the weight of the obtained residue is 11.1 g. It is extracted by 2×100 ml of hot heptane, the heptane is distilled off and the remaining 8.3 g of crude 2-difluoro-chloro-methyl-8-trifluoro-methyl-4-chloro-quinoline are recrystallized from aqueous methanol.

Yield: 6.8 g, m.p.: 37°–39° C.

EXAMPLE 9

2,8-bis(Trifluoromethyl)-4-chloro-quinoline

A mixture of 65 g of antimony-trifluoride and 10 ml of antimony-pentachloride is stirred at a temperature of 150° C. for 20 minutes, then recooled to 60° C. and under constant cooling 40 g of 2,8-bis(trichloromethyl)-4-chloro-quinoline are added. It is stirred at a temperature of 60°–70° C. for 5 minutes, then the melt is poured into 200 ml of intensely stirred, cooled, carbon tetrachloride. The antimony halogenides are filtered off, the organic phase is washed with thin hydrochloric acid, dried, filtered and evaporated.

Yield: 26.2 g, m.p.: 40°–42° C.

EXAMPLE 10

100 ml of dichloromethane are cooled to −10° C. and 20 ml of antimony-pentafluoride are added to the obtained mixture 40 g of 2,8-bis(trichloromethyl)-4-chloro-quinoline dissolved in 100 ml of dichloromethane are dropped at a temperature of −5° to −10° C. The mixture is stirred for 4 hours, allowed to warm to room temperature whereupon 700 ml of 10 percent hydrochloric acid are added. It is stirred for 15 minutes, the two phases are separated, the aqueous phase is extracted with 2×500 ml of dichloromethane. The combined organic phase is filtered, dried, evaporated. 32 g of a brown syrup are obtained which are purified by from 600 ml of hexane filtering it on carbon.

Yield: 22.6 g, m.p.: 42°–44° C.

EXAMPLE 11

Into a Hasteloy-C pressure-tight autoclave of 1 liter, equipped with a mixture, 398.3 g of 2,8-bis(trichloromethyl)-4-chloro-quinoline, 250 ml of anhydrous hydrogen fluoride and 20 ml of antimony-pentachloride are added. The reaction mixture is heated up to 170°–180° C. under constant stirring and slow but steady blowing off the hydrochloric acid gas. The mixture is stirred at this temperature for 36 hours. The mixture is recooled, the hydrogen fluoride is distilled off, the residue is partitioned between 1 liter of dichloromethane and 500 ml of saturated aqueous solution of sodium-carbonate. The organic phase is washed with 2×100 ml of water, dried, evaporated. The residue is purified by vacuum distillation.

Yield: 264.6 g, m.p.: 45°–46° C., b.p.$_{18}$ 148°–152° C.

EXAMPLE 12

39.83 g (0.1 mole) of 2,8-bis(trichloromethyl)-4-chloro-quinoline are dissolved in 70 ml of dry dichloromethane. Under constant stirring the solution is cooled to −50° C. whereupon 10 ml of antimony-pentafluoride are dropped to the obtained suspension at a temperature of −5° to 0° C. within 60 minutes. It is stirred at 0° to 5° C. for further 2 hours, then the reaction mixture is admixed with icy concentrated hydrochloric acid. The two phases are separated, the organic phase is washed with water, dried, evaporated. 30.6 g residue are fractionated in vacuum. The main fraction is distilled at 17–19 torr at a temperature of 150°–158° C. The distillatum solidifies while standing.

Yield: 26.4 g, 88.1%, m.p.: 44°–46° C.

Following compounds may be prepared the same way:
2,7-bis(Trifluoromethyl)-4-chloro-quinoline m.p.: 35°–37° C.
2,6-bis(Trifluoromethyl)-4-chloro-quinoline liquid
2,5-bis(Trifluoromethyl)-4-chloro-quinoline liquid
2,8-bis(Trifluoromethyl)-4,5-dichloro-quinoline m.p. 52°–54° C.

EXAMPLE 13

Proceeding as described in Example 6 following products may be obtained:
2-trichloromethyl-4-chloro-6-trifluoromethyl-quinoline, melting point: 46°–48° C.,
2-trichloromethyl-4-chloro-7-trifluoromethyl-quinoline, melting point: 70°–73° C.,
2-trichloromethyl-4-chloro-5-trifluoromethyl-quinoline, melting point: 63°–67° C.,
2-trichloromethyl-4-bromo-8-trifluoromethyl-quinoline, melting point: 73°–75° C.

We claim:
1. A process for the preparation of a compound of the formula (I)

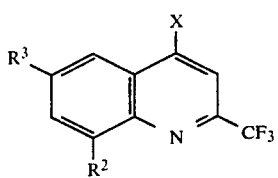

wherein
 $R^2$ is trifluoromethyl or chloro;
 $R^3$ is hydrogen or chloro; and
 X is halogen,
which comprises the step of fluorinating a compound of the formula (II)

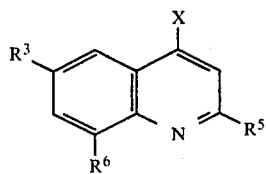

wherein
 $R^5$ is —CFCl$_2$, —CF$_2$Cl or —CCl$_3$; and
 $R^6$ is chloro or trichloromethyl, with a mixture of antimony(III)fluoride and antimony(V)chloride or a mixture of antimony(III)fluoride and antimony(V)bromide wherein the molar ratio of antimony(III) to antimony(V) is 1–5:1 and the ratio of fluorine-chlorine or fluorine-bromine is 0.8 to 3.0 and the fluorine content of the reagent, related to the halogen atom, is 1.1 to 2.8 molar equivalent at 40° to 180° C.

2. The process defined in claim 1 wherein the starting material of the Formula (II) is 2,8-bis-(trichloromethyl)-4-chloro-quinoline and the product of the Formula (I) is 2,8-bis-(trifluromethyl)-4-chloro-quinoline and wherein the fluorination of the compound of the Formula (II) is carried out with a mixture of antimony(III)fluoride and antimony(V)chloride.

3. A process for the preparation of a compound of the formula (I)

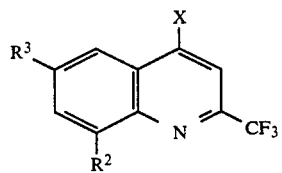

wherein
 $R^2$ is trifluoromethyl or chloro;
 $R^3$ is hydrogen or chloro; and
 X is halogen,
which comprises the step of fluorinating a compound of the formula (II)

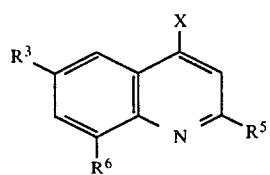

wherein
 $R^5$ is —CFCl$_2$, —CF$_2$Cl or —CCl$_3$; and
 $R^6$ is chloro or trifluoromethyl, with antimony(V)-fluoride at a temperature of −20° to 30° C. wherein the fluoride is used in a quantity of 0.25 to 0.38 moles related to the chlorine atoms to be replaced in the halomethyl groups of the compounds of the formula (II).

4. A process for the preparation of a compound of the formula (I)

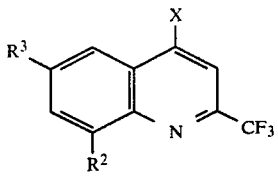

wherein
 $R^2$ is trifluoromethyl or chloro;
 $R^3$ is hydrogen or chloro; and
 X is halogen,
which comprises the step of fluorinating a compound of the formula (II)

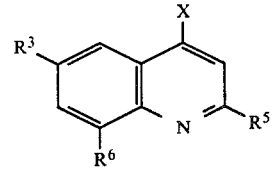

wherein
 $R^5$ is —CFCl$_2$, —CF$_2$Cl or —CCl$_3$; and
 $R^5$ is chloro or trichloromethyl, with antimony(V)-chloride and hydrogen fluoride at a temperature of −10° to 180° C., wherein the hydrogen fluoride is employed in dry form and used as both a fluorinating agent and as a solvent in a quantity of 2 to 10 molar equivalents related to the replaced hydrogen atoms, while the formed hydrogen halide is blown off.

* * * * *